United States Patent [19]
Sakakura et al.

[11] Patent Number: 5,910,607
[45] Date of Patent: Jun. 8, 1999

[54] PROCESS FOR PRODUCING ACRYLIC ACID

[75] Inventors: Yasuyuki Sakakura; Masahiko Yamagishi; Hirochika Hosaka, all of Yokkaichi, Japan

[73] Assignee: Mitsubishi Chemical Corp., Tokyo, Japan

[21] Appl. No.: 08/508,697

[22] Filed: Jul. 28, 1995

[30] Foreign Application Priority Data

Aug. 4, 1994 [JP] Japan .................................. 6-201522

[51] Int. Cl.⁶ ...................... C07C 51/21; C07C 51/235
[52] U.S. Cl. ........................................... 562/532; 562/545
[58] Field of Search ..................................... 562/532, 545

[56] References Cited

U.S. PATENT DOCUMENTS

| | | | |
|---|---|---|---|
| 3,689,541 | 9/1972 | Sennewald et al. | 260/526 N |
| 3,781,193 | 12/1973 | Sennewald et al. | 203/8 |
| 3,844,903 | 10/1974 | Willersinn et al. | 203/51 |
| 4,317,926 | 3/1982 | Sato et al. | 562/532 |
| 5,315,037 | 5/1994 | Sakamoto et al. | 562/545 |

FOREIGN PATENT DOCUMENTS 2 146 636  4/1985  United Kingdom .

*Primary Examiner*—Paul J. Killos
*Assistant Examiner*—Rosalynd Keys
*Attorney, Agent, or Firm*—Armstrong, Westerman, Hattori, McLeland & Naughton

[57] ABSTRACT

In a process for producing acrylic acid, wherein propylene and/or acrolein is catalytically oxidized with molecular oxygen in a vapor phase and the gas resulting from the oxidation is cooled and/or absorbed in water to form a crude aqueous acrylic acid, followed by azeotropic distillation to remove the water with an entrainer of a boiling point of no higher than 130° C. on the crude aqueous acrylic acid which may have, upon necessity, undergone removal of aldehydes contained therein to produce acrylic acid purified in that the crude aqueous acrylic acid is substantially dehydrated, the improvement which comprises conducting the azeotropic distillation under such conditions that concentrations of the entrainer and water in the bottom product of the azeotropic distillation are from 5% to 30% by weight and no higher than 0.5% by weight, respectively, where the theoretical number of plates in the azeotropic distillation column for dehydration used and that in the distillation column for separating acetic acid used are preferably from 5 to 20. Highly-purified acrylic acid can thus be obtained from the crude aqueous acrylic acid without causing unfavorable polymerization of acrylic acid.

18 Claims, 1 Drawing Sheet

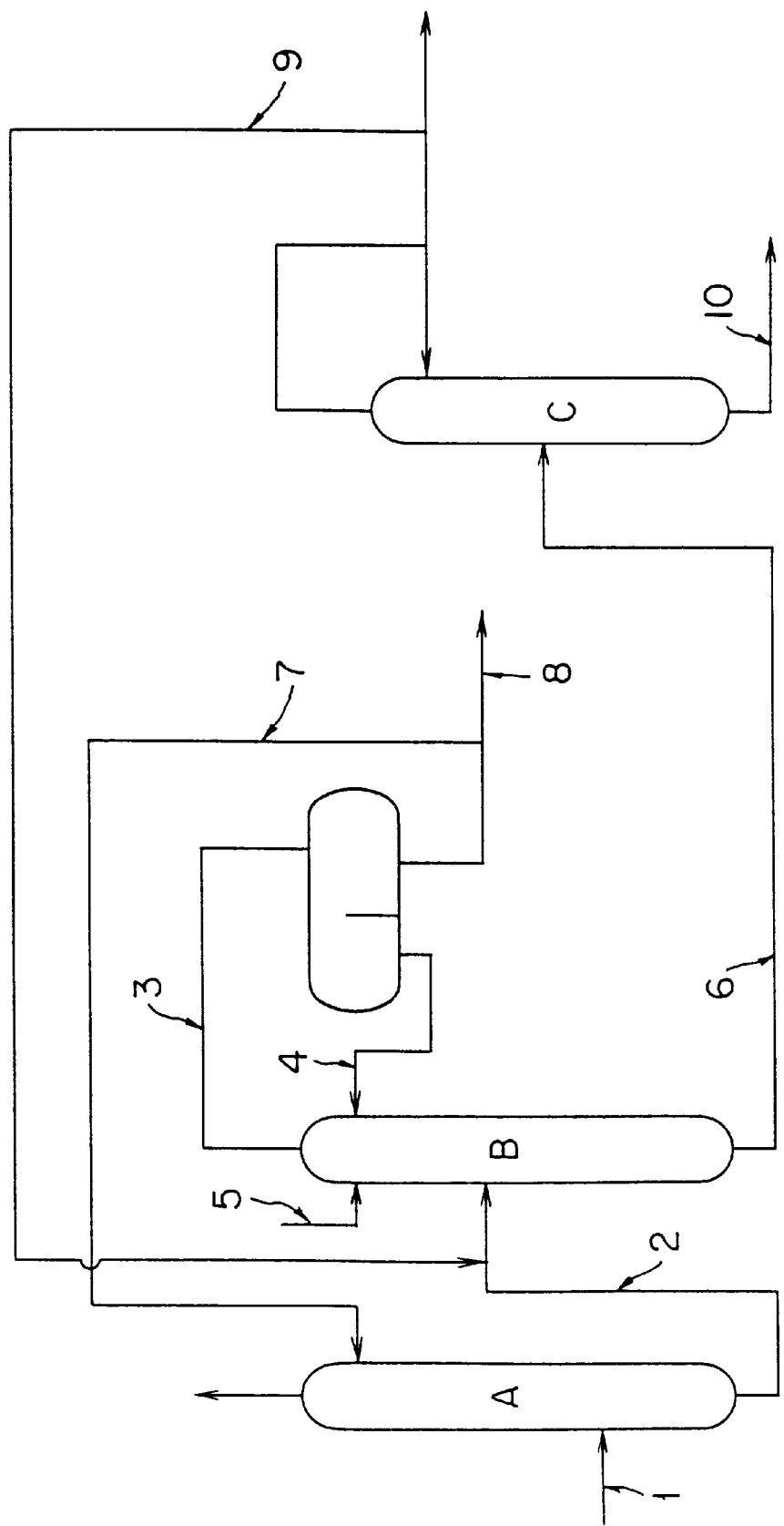
FIG. I

PROCESS FOR PRODUCING ACRYLIC ACID

BACKGROUND OF THE INVENTION

1. Field of the Invention

The present invention relates to a process for obtaining purified acrylic acid from a crude aqueous acrylic acid, wherein the polymerization of acrylic acid is prevented. More specifically, the present invention relates to a process for obtaining highly-purified acrylic acid through distillation, wherein the polymerization of acrylic acid which tends to be caused in a distillation column is prevented when impurities having a lower boiling point, such as water and acetic acid, are removed by using an entrainer from a crude aqueous acrylic acid which is obtained from the catalytic oxidation of propylene and/or acrolein with molecular oxygen, conducted in a vapor phase.

2. Related Art

When a gas resulting from the vapor-phase oxidation of propylene and/or acrolein with a molecular-oxygen-containing gas, carried out in the presence of steam by the use of an oxidation catalyst is cooled and/or absorbed in water, a crude aqueous acrylic acid can be obtained. This crude aqueous acrylic acid contains not only acrylic acid but also some by-products such as acetic acid, formic acid, formaldehyde and acetaldehyde. When the degree of conversion of the oxidation reaction is low, the crude aqueous acrylic acid contains a small amount of unconverted acrolein used or formed. In such a case, the acrolein is removed from the crude aqueous acrylic acid by means of stripping or the like, and the resultant is subjected to purification to obtain purified acrylic acid.

The concentration of acrylic acid in the crude aqueous acrylic acid thus obtained is from 40% to 80% by weight. Among the by-products, the most important is acetic acid, and the crude aqueous acrylic acid contains from 1% to 5% by weight of acetic acid. It is not efficient to directly separate water, acetic acid and acrylic acid in the crude aqueous acrylic acid by distillation because of their chemical similarity and physicochemical properties such as vapor-liquid equilibriums. With respect to a method for obtaining purified acrylic acid, there have been proposed, in recent years, a number of processes which comprise the step of efficiently removing water by azeotropic distillation with an entrainer used, and the step of separating acetic acid by distillation. According to our classification, there are two types of processes for separating water and acetic acid, that is, a process which may be called "one-column process", wherein water and acetic acid are simultaneously removed from acrylic acid by using only one distillation column (Japanese Patent Publications Nos. 18967/1971, 20372/1971, 22456/1971, 34692/1971 and 21124/1974, and Japanese Laid-Open Patent Publication No. 246941/1993), and a process called "two-column process", in which dehydration and the separation of acetic acid are separately conducted by using two different distillation columns (Japanese Patent Publications Nos. 15569/1966, 18966/1971, 25451/1975 and 10691/1988, Japanese Laid-Open Patent Publication No. 181440/1991, and Japanese Patent Publications Nos. 15495/1994 and 15496/1994). The present invention concerns improvements in the two-column process.

In the former process, that is, in the one-column process, water and acetic acid are simultaneously removed by the use of only one column. It is therefore necessary to use a distillation column having a large theoretical number of plates, and a high reflux ratio is required also. When a distillation column having a large number of plates is used, the pressure at the bottom of the column may as the result be excessively high, so that it may be difficult to keep the temperature of the bottom product low. The use of such a distillation column is thus disadvantageous from the standpoint of energy consumption. In addition, acrylic acid is a material which is polymerized very easily, so that it is a fatal shortcoming from the viewpoint of prevention of the polymerization of acrylic acid that the bottom of the column reaches an excessively high temperature.

In the two-column purification process, water and acetic acid are respectively removed from acrylic acid by using two different distillation columns designed respectively therefor. Therefore, a column optimized and suitable for dehydration and one optimized and suitable for the separation of acetic acid can be respectively used. This process is thus advantageous as a whole from the viewpoint of energy even though two columns are used. Further, this two-column process is also advantageous in that acetic acid, which is a main by-product of the oxidation reaction of propylene and/or acrolein, can be separated and recovered from the overhead product of the acetic-acid-separating distillation column.

SUMMARY OF THE INVENTION

We made studies for the conditions of distillation conducted by using an azeotropic distillation column for dehydration and an distillation column for separating acetic acid which are used in the two-column process for obtaining purified acrylic acid. In the course of these studies, we found that the polymerization of acrylic acid tends to occur, in particular, in the vicinity of the bottom of the azeotropic distillation column for dehydration. We therefore examined various distillation conditions in order to eliminate the shortcoming in that the azeotropic distillation column for dehydration will not be continuously operated for a long time due to polymers of acrylic acid deposited at the bottom of the distillation column. As a result, it was found that the unfavorable polymerization of acrylic acid which tends to take place in the azeotropic distillation column for dehydration can be prevented by controlling the concentrations of water and an entrainer in the bottom product of the distillation column. The present invention has been accomplished on the basis of this finding.

An object of the present invention is to provide an industrial process for obtaining purified acrylic acid, wherein propylene and/or acrolein is catalytically oxidized in the gas or vapor phase with a molecular-oxygen-containing gas in the presence of steam, the gas resulting from the oxidation is cooled and/or absorbed in or scrubbed with water to form a crude aqueous acrylic acid, and the crude aqueous acrylic acid is dehydrated by azeotropic distillation with an entrainer by using an azeotropic distillation column for dehydration under the conditions which are improved in order to prevent the unfavorable polymerization of acrylic acid to be caused in the distillation column. Another object of the present invention is to provide an industrially advantageous process, wherein the overhead product of the azeotropic distillation column for dehydration is divided into two phases, that is, an aqueous phase containing the whole amount of the water and the whole amount of or a portion of the acetic acid, the water and the acetic acid being those originally contained in the crude aqueous acrylic acid, in one hand, and an entrainer phase, in another hand, and the whole amount of the entrainer phase is returned to the azeotropic distillation column for dehydration as reflux, while the aqueous phase is re-used as the water for scrubbing in which the gas resulting from the oxidation is absorbed.

The present invention and the preferred embodiments thereof are as follows:

1. In a process for producing acrylic acid, wherein propylene and/or acrolein is catalytically oxidized with molecular oxygen in a vapor phase and the gas resulting from the oxidation is cooled and/or absorbed in or scrubbed with water to form a crude aqueous acrylic acid, followed by azeotropic distillation for dehydration to remove water with an entrainer of a boiling point of no higher than 130° C. on the crude aqueous acrylic acid which may have, upon necessity, undergone removal of aldehydes contained therein to produce acrylic acid purified in that the crude aqueous acrylic acid is substantially dehydrated, the improvement which comprises conducting the azeotropic distillation under such conditions that concentrations of the entrainer and water in the bottom product of a distillation column for the azeotropic distillation for dehydration are from 5% to 30% by weight and no higher than 0.5% by weight, respectively.

2. The process for producing acrylic acid according to item 1, wherein the concentration of the entrainer in the bottom product of the azeotropic distillation column for dehydration is from 6 to 15% by weight.

3. The process for producing acrylic acid according to item 1 or 2, wherein the concentration of the water in the bottom product of the azeotropic distillation column for dehydration is from 0.05 to 0.3% by weight.

4. The process for producing acrylic acid as set forth in any one of the items 1 to 3, wherein the bottom product of the azeotropic distillation column for dehydration is subjected to separation therefrom of lower-boiling materials including acetic acid and the entrainer as a overhead product in a distillation column, which column will be hereinbelow referred to as a distillation column for separating acetic acid, thereby to obtain acrylic acid as the bottom product of the distillation column for separating acetic acid, the overhead product being returned to the azeotropic distillation column.

5. The process for producing acrylic acid as set forth in any one of the item 1 to 4, wherein the entrainer is azeotropically distilled with both water and acetic acid, and has a boiling point of 80 to 130° C.

6. The process for producing acrylic acid as set forth in any one of the items 1 to 5, wherein the temperature at the bottom of the azeotropic distillation column for dehydration and the temperature at the bottom of the distillation column for separating acetic acid are no higher than 100° C.

7. The process for producing acrylic acid as set forth in any one of the items 1 to 6, wherein the pressure at the top of the azeotropic distillation column for dehydration is 100 to 300 mmHg, and the pressure at the top of the distillation column for separating acetic acid is 50 to 200 mmHg.

8. The process for producing acrylic acid as set forth in any one of the items 1 to 7, wherein the theoretical number of plates of the azeotropic distillation column for dehydration and that of the distillation column for separating acrylic acid are respectively 5 to 20.

9. The process for producing acrylic acid as set forth in any one of the items 1 to 8, wherein the crude aqueous acrylic acid fed to the azeotropic distillation column for dehydration contains 40% to 80% by weight of acrylic acid, 1% to 5% by weight of acetic acid, and 20% to 60% by weight of water.

10. The process for producing acrylic acid as set forth in any one of the item 1 to 9, wherein the overhead product of the azeotropic distillation column for dehydration, containing substantially the whole amount of the water, a portion of or the whole amount of the acetic acid, the water and the acetic acid being those originally contained in the crude aqueous acrylic acid, and the entrainer is separated into two phases, that is, an entrainer phase and an aqueous phase, and the whole amount of the entrainer phase is returned to the azeotropic distillation column for dehydration as reflux, while a portion of or the whole amount of the aqueous phase is re-used as the water for scrubbing in which the gas resulting from the oxidation reaction is absorbed.

The present invention is thus concerned with a process for purifying a crude aqueous acrylic acid which is obtained by the cooling and/or scrubbing with water of the gas resulting from the catalytic oxidation of propylene and/or acrolein with molecular oxygen, conducted in a vapor phase. When impurities having a lower boiling point, such as water and acetic acid, are removed from the crude aqueous acrylic acid by the use of an entrainer, the concentrations of water and the entrainer in the bottom product of the azeotropic distillation column for dehydration are properly controlled whereby the polymerization of acrylic acid to be otherwise caused in the distillation column is prevented resulting in the production of highly-purified acrylic acid.

By the present invention, it is made possible to stably and continuously operate the azeotropic distillation column and the distillation column for separating acetic acid for a long period of time, and highly-purified acrylic acid which can be suitably used as the starting material in the production of an acrylic acid ester can be obtained with industrial advantages.

BRIEF DESCRIPTION OF THE DRAWING

The sole FIGURE is a flow chart showing an embodiment of the present invention.

DESCRIPTION OF THE PREFERRED
EMBODIMENT OF THE INVENTION

Outline of the Production of Purified Acrylic Acid

In the production of acrylic acid in which propylene and/or acrolein is catalytically oxidized in a vapor phase with molecular oxygen, a crude aqueous acrylic acid is obtained when the gas resulting from the oxidation reaction is cooled and/or scrubbed with or absorbed in water. The crude aqueous acrylic acid thus formed contains not only acrylic acid but also some by-products such as acetic acid, formic acid, formaldehyde and acetaldehyde. When the degree of conversion of the oxidation reaction is low, the crude aqueous acrylic acid is to contain a small amount of unconverted acrolein, so that the acrolein is removed by means of stripping or the like, if necessary. The crude aqueous acrylic acid (in this Specification, the term "crude aqueous acrylic acid" includes one which has been subjected to preliminary treatment such as the removal of acrolein) is then subjected to purification comprising at least dehydration, thereby obtaining purified acrylic acid. Specifically, the crude aqueous acrylic acid is subjected to dehydration by azeotropic distillation with an entrainer in the azeotropic distillation column for dehydration, and substantially the whole amount of the water, formic acid and formaldehyde, and a portion of the acetic acid are removed from the crude aqueous acrylic acid as the overhead product of the azeotropic distillation column for dehydration. Thus, acrylic acid containing as an impurity the remaining portion of the acetic acid which has been contained in the crude aqueous acrylic acid is obtained as the bottom product. The bottom product is subsequently treated in the distillation column for separating acetic acid, whereby the acetic acid and the entrainer are removed as a distillate. The whole amount of or a portion of the distillate is recirculated in the above azeotropic distillation column for dehydration, and treated again to separate and recover the acrylic acid contained in the distillate. Purified acrylic acid can be obtained as the bottom product of the acetic-acid-separating distillation column. The purified acrylic acid is utilized as acrylic acid, or introduced to the next step for esterification to obtain an acrylic acid ester.

Acrylic acid is a material which is polymerized very easily. It is therefore well known to those skilled in the art that polymers of acrylic acid are often produced in a column for distillation of a acrylic acid to make the further operation of the column impossible. We found that unfavorable polymers of acrylic acid tend to be produced in the vicinity of the bottom of the azeotropic distillation column for dehydration, and in the vicinity of the top of the distillation column for separating acetic acid, after these distillation columns are continuously operated. Therefore, we variously changed the conditions of distillation conducted by using these distillation columns. As a result, by controlling the concentrations of the entrainer and water in the bottom product of the azeotropic distillation column to no lower than 5% by weight but no higher than 30% by weight, and no higher than 0.5% by weight, respectively, it was found possible to successfully prevent the unfavorable polymerization of acrylic acid to be caused not only in the azeotropic distillation column for dehydration but also in the distillation column for separating acetic acid, and it was thus made possible to continuously operate these distillation columns for a long period of time.

The Gas to be Treated

In the industrial production of acrylic acid, wherein propylene and/or acrolein is catalytically oxidized with a molecular-oxygen-containing gas in a vapor phase mostly in the presence of steam, the crude aqueous acrylic acid obtained by cooling the gas resulting from the oxidation, and/or by scrubbing with or absorbing in water contains 40% to 80% by weight of acrylic acid, 1% to 5% by weight of acetic acid and 20% to 60% by weight of water. The amount of the water which is used for the absorption of the gas conducted in an acrylic-acid-absorbing/scrubbing column is important from the economical point of view.

When the amount of the water used for the absorption of the gas is increased, the concentration of acrylic acid in the crude aqueous acrylic acid is lowered. As a result, the load on the azeotropic distillation column for dehydration is increased.

Azeotropic Dehydration

It is preferable that the concentration of the entrainer in the bottom product of the azeotropic distillation column be high from the viewpoint of prevention of the polymerization of acrylic acid. However, when this concentration is excessively high, an increased amount of energy is needed for the separation of the entrainer from the bottom product of the azeotropic distillation column for dehydration, conducted in the distillation column for dehydration. Such an excessively high concentration is thus economically disadvantageous. Moreover, in this case, acrylic acid, the final product, may be contaminated with the entrainer, so that the entrainer may reduce purity of acrylic acid and could inhibit polymerization of the acrylic acid to produce a water-soluble polymer after those substances which have a high boiling point, such as a polymerization inhibitor, have been removed from the acrylic acid. The concentration of the entrainer in the bottom product is preferably in such a level that may not interfere with the separation of acetic acid which is conducted in the distillation column for separating acetic acid. In effect, however, the concentration of the entrainer also depends on whether the entrainer and acetic acid can be azeotropically distilled or not. In the result, the concentration of the entrainer in the bottom product is controlled to preferably 5% by weight or more but 30% by weight or less, in general, in the range of 6% to 15% by weight, more preferably in the range of 6% to 13% by weight. When the concentration of the entrainer is insufficient, it is also possible to feed an additional amount of the entrainer to the distillation column for separating acetic acid.

The present invention also calls for another requirement to be met. In order to fulfill the other essential condition of the operation of the azeotropic distillation column for dehydration, the concentration of water in the bottom product of the azeotropic distillation column for dehydration, is controlled to 0.5% by weight or less. This can be attained by controlling the amount of the entrainer phase returned as reflux to the azeotropic distillation column for dehydration, and the amount of heat corresponding thereto, supplied by a reboiler. The concentration of water in the bottom product can be made low by increasing the amount of evaporation at the reboiler and the amount of the entrainer phase returned as reflux. For the purpose of attaining the object of the present invention, that is, preventing the polymerization of acrylic acid, the concentration of water in the bottom product is controlled to 0.5% by weight or less, preferably 0.3% to 0.05% by weight. When the concentration of water is made excessively low, the bottom of the azeotropic distillation column for dehydration reaches a high temperature, which is unfavorable for the purpose of preventing the polymerization of acrylic acid. Further, when the concentration of water is excessively low, it is necessary to return, as reflux, an increased amount of the entrainer phase to the azeotropic distillation column for dehydration, and the overhead product is to contain such an increased amount of acetic acid that only a decreased amount of acetic acid can be recovered from the overhead product of the distillation column for separating acetic acid.

Besides the condition that the entrainer be azeotropically distilled with water, it is important that the entrainer is an organic solvent having a normal boiling point of 130° C. or lower, preferably in the range of 80 to 130° C. When the boiling point of the entrainer is higher than 130° C., the separation between the entrainer and acrylic acid may not be conducted easily in the distillation column for separating acetic acid. For this reason, the entrainer tends to remain in the bottom product, and the purified acrylic acid is contaminated with the entrainer. Thus, the acrylic acid would suffer from lower purity. On the other hand, when the boiling point of the entrainer is lower than 80° C., the degree of vacuum in the azeotropic distillation column for dehydration cannot be made high, so that the top of the distillation column reaches a high temperature resulting in the polymerization of acrylic acid liable to take place more easily.

Specific examples of the entrainer include toluene, heptane, cyclohexane, methylcyclohexane and isobutyl ether. These entrainers may be azeotropically distilled not only with water but also with acetic acid, so that they have an effect of making easy the separation of acetic acid, conducted in the azeotropic distillation column for dehydration and in the distillation column for separating acetic acid. These entrainers can therefore make the reflux ratio low; low reflux ratios are economically advantageous. It is also possible to use such an organic solvent that is not azeotropically distilled with acetic acid but with water, for example, n-butyl acetate, isobutyl acetate, iso-propyl acetate and methyl isobutyl ketone. When such an organic solvent that is not azeotropically distilled with acetic acid is used as the entrainer, it would be necessary to return, as reflux, a large amount of the entrainer phase to the azeotropic distillation column for dehydration in order to effect the separation of acetic acid there without any other measures for separatiing acetic acid. It is therefore unfavorable to recirculate, in the azeotropic distillation column for dehydration, the whole amount of the overhead product of the distillation column for separating acetic acid. It is favorable to introduce the overhead product to the step of the recovery of acetic acid, thereby separating and recovering acetic acid. The above-mentioned entrainers can be used either singly or, of course, in combination.

Distillation for Separating Acetic Acid

The bottom product of the azeotropic distillation for dehydration which has substantially all of water in the crude aqueous acrylic acid removed will then be subjected to distillation for separating acetic acid from the acrylic acid, whereby acrylic acid is obtained as a bottom product while lower-boilers such as acetic acid and the entrainer will be removed from the top.

The distillation column can be a conventional one provided that it has "theoretical plates" required for effecting the distillation of the nature given above.

Operation of the Distillations

The temperature of the bottom product of the azeotropic distillation column for dehydration and that of the bottom product of the distillation column for separating acetic acid are preferably no higher than 100° C. These distillation columns are operated, in general, under reduced pressure, and the temperatures of the bottom products thereof can each be controlled by controlling each of the pressure at the top thereof. The pressure at the top of the azeotropic distillation column for dehydration is usually controlled to 100 to 300 mmHg, and the distillation column usually has 30 to 50 plates when it is a plate column or usually from 5 to 20 plates when expressed in the theoretical number of plates. The pressure at the top of the distillation column for separating acetic acid is usually controlled to 50 to 200 mmHg, and a distillation column having, in general, 15 to 50 plates (the theoretical number of plates usually: 5 to 20), preferably 30 to 40 plates (the theoretical number of plates usually: 10 to 15) is used. These distillation columns are not limited to plate columns, and packed columns and any other distillation columns can also be used provided that they have theoretical numbers of plates required for effecting the distillation desired.

For the purpose of preventing the unfavorable polymerization of acrylic acid, it may be a common practice to operate the distillations in the presence of a polymerization inhibitor added such as a phenol or amine polymerization inhibitor e.g. hydroquinone, hydroquinone monomethyl ether or phenothiazine, which is often supplied along with a solution of acrylic acid, the entrainer and water from the top of the distillation columns. Further, for the same purpose, a molecular-oxygen-containing gas is blown into the distillation columns from the bottom thereof.

The overhead product of the azeotropic distillation column for dehydration is an aqueous solution containing the whole amount of or a portion of the acetic acid which has been originally contained in the crude aqueous acrylic acid, and a small amount of formic acid and formaldehyde. This aqueous solution is effectively used when it is returned to the above-described scrubbing process for the vapor phase oxidation gas to use as the water for the absorption of, among others, acrylic acid in the gas. In the case where the aqueous solution contains an entrainer, it can be recycled to the scrubbing process if it is subjected beforehand to distillation to remove the entrainer therefrom, and then cooled. When the entrainer used is such a hydrocarbon that is substantially insoluble in water, for example, toluene, heptane or cyclohexane, the entrainer can easily be removed by decantation from the overhead distillate of the azeotropic distillation column for dehydration.

It is preferable that the concentration of acrylic acid in the aqueous distillate of the azeotropic distillation for dehydration be 1% by weight or less. When the aqueous distillate contains a large amount of acrylic acid due to insufficient separation efficiency of the azeotropic distillation column for dehydration, a loss of acrylic acid may be incurred. However, if the aqueous distillate is re-used as the water for scrubbing the vapor phase oxidation product, a portion of the acrylic acid contained in the aqueous distillate can be recovered at the bottom of the scrubbing column.

Representative Embodiment

A representative embodiment of the present invention will now be explained by referring to the flow chart shown in the FIGURE. However, the technical scope of the present invention is not limited by this flow chart nor by the following description.

The gas resulting from catalytic oxidation of propylene and/or acrolein with a molecular-oxygen-containing gas, conducted in a vapor phase in the presence of steam, is fed through line 1 to a scrubbing column A for absorbing acrylic acid, and brought into contact with water which is introduced to the column A through line 7, whereby acrylic acid is absorbed in the water. A crude aqueous acrylic acid can thus be obtained as the bottom product of the column A for absorbing acrylic acid. In general, in order to improve the efficiency of the absorption of acrylic acid, the bottom product drawn by the line 2 is often partly cooled and recirculated in the column A for absorbing acrylic acid(not shown in the FIGURE). It is preferable to use the overhead product of an azeotropic distillation column B for dehydration as the water for the absorption of acrylic acid, which is supplied to the column A through the line 7 as shown in the FIGURE, in order to reduce as much as possible the amount of water which is drained. Besides acrylic acid, the crude aqueous acrylic acid may contain by-products of the oxidation reaction such as acetic acid, formic acid and formaldehyde, and acrolein. Therefore, if necessary, the crude aqueous acrylic acid may be fed to an acrolein-evaporating column to remove the acrolein therefrom (not shown in the FIGURE).

The crude aqueous acrylic acid, which is the bottom product of the column A for absorbing acrylic acid, is introduced through line 2 to the azeotropic distillation column B for dehydration. An entrainer is introduced through line 5 to the azeotropic distillation column B for dehydration, and azeotropic distillation is conducted. The distillate obtained by cooling and condensing the vapor discharged from the top of the distillation column B, containing the entrainer, water, and the whole amount of or a portion of the acetic acid which has been contained in the crude aqueous acrylic acid is subjected to phase separation or decantation when the entrainer used is insoluble in water. The whole amount of the entrainer phase thus recovered is returned through line 4 to the distillation column B as reflux. The aqueous phase is drawn out, and sent through line 7 to and re-used in the column A for absorbing acrylic acid. It is also possible that a portion of the aqueous phase is drawn out through line 8 and discarded in order to balance the amount of water in the system. In order to control, in particular, the concentration of water in the bottom product of the azeotropic distillation column B for dehydration, the amount of the entrainer phase to be returned as reflux is controlled. The amount of the entrainer phase to be returned depends on the azeotropic composition of water and the entrainer. The concentration of water in the bottom product is thereby controlled to 0.5% by weight or less, preferably 0.3% to 0.05% by weight; the concentration of the entrainer in the bottom product is controlled to 5% to 30% by weight, preferably 6% to 15% by weight, more preferably 6% to 13% by weight.

The bottom product of the azeotropic distillation column B for dehydration is fed through line 6 to an distillation column C for separating acetic acid. In this distillation column C, substantially all of those impurities which have a lower boiling point are removed as overhead products, and purified acrylic acid is obtained as the bottom product, which will be withdrawn through line 10. The purified acrylic acid can be introduced, when necessary, to a subsequent step (not shown in the FIGURE), where it is used, for example, as the starting material of an acrylic acid ester.

The overhead distillate essentially consisting of acetic acid, the entrainer and acrylic acid, obtained from the top of the distillation column C for separating acetic acid is returned through line 9 to and recirculated in the azeotropic distillation column B for dehydration so as to recover the acrylic acid contained therein. Alternatively, the distillate is fed to a step for the separation and recovery of acetic acid (not shown in the FIGURE), thereby obtaining purified acetic acid. The acrylic acid and the entrainer separated in this step can also be returned to the azeotropic distillation column B for dehydration.

The temperature of the bottom product of each of the distillation columns is controlled to 100° C. or lower.

The present invention will now be explained more specifically by referring to the following examples.

EXAMPLE 1

Dehydration distillation of an aqueous acrylic acid was conducted by using a glass-made laboratory distillation device. In the distillation device, a distillation column, which was a glass-made cylinder having a diameter of 50 mm, was equipped with a 1-liter flask serving as a reboiler at the bottom thereof, and with a condenser at the top thereof. The outlet of the condenser was connected to a vacuum equipment. The distillation column was filled with Raschig rings of 3 mm to a height of 90 cm. This height corresponds to a theoretical number of plates of 15. The distillate condensed by the condenser provided at the top of the column was subjected to phase separation by using a decanter. Thereafter, the whole amount of the entrainer phase was returned to the column as reflux, and the aqueous phase was drawn out. The flask, the reboiler, was heated in an oil bath. The flask was dipped in the oil bath, and the amount of heat was adjusted by controlling the temperature of the oil. The bottom product was drawn out from the flask by using a pump so as to keep the liquid level in the flask constant.

The aqueous acrylic acid used as the starting solution for distillation contained 55% by weight of acrylic acid, 1.5% by weight of acetic acid, 0.3% by weight of formaldehyde, and a small amount of formic acid. By using toluene as the entrainer, an azeotropic dehydration distillation test was carried out. The aqueous acrylic acid and toluene were fed to the distillation column from the middle level thereof at a feed rate of 280 g/hour and 14 ml/hour, respectively. The pressure was adjusted to 180 mmHg. Hydroquinone and phenothiazine were supplied as polymerization inhibitors from the top of the column. Air was fed to the flask placed at the bottom of the column at a feed rate of 15 ml/hour. The amount of the polymerization inhibitors supplied were controlled so that the concentrations of hydroquinone and phenothiazine in the bottom product would be 800 ppm and 500 ppm, respectively.

The azeotropic distillation column for dehydration was continuously operated for 7 hours. The temperature at the top of the column was 49° C., that of the bottom product was 90° C., and the amount of the entrainer phase returned to the top of the column as reflux was 830 ml. When the distillation became steady, acrylic acid drawn out from the bottom of the column was analyzed by gas chromatography. As a result, the acrylic acid was found to contain 2.3% by weight of acetic acid, 0.5% by weight of water, 7% by weight of toluene, and the polymerization inhibitors. The acrylic acid was drawn out from the bottom of the column at a rate of 170.5 g/hour on an average. The aqueous phase obtained, as a distillate, from the top of the column was found to contain 0.2% by weight of acetic acid, 0.1% by weight of acrylic acid, formaldehyde and formic acid.

When 7 hours passed after the distillation became steady, the distillation was suspended, and the inside of the distillation device was observed. As a result, polymers of acrylic acid were found neither in the flask serving as the reboiler nor on the surface of the packing housed in the distillation column.

EXAMPLES 2 to 4, and COMPARATATIVE EXAMPLES 1 to 3

An azeotropic dehydration distillation test was carried out in the same manner as in Example 1, provided that the amount of toluene supplied as the entrainer and that of the entrainer phase returned to the distillation column as reflux were varied so as to change the concentration of toluene in the bottom product. When 7 hours passed after the distillation became steady, the test was suspended, and the distillation device was disjointed. The inside of the flask serving as the reboiler, and the packing at the lower part of the distillation column were particularly observed as to whether polymers of acrylic acid had been produced or not.

The composition of the water and the entrainer contained in the bottom product, the temperature of the bottom product, and the results of the above-described observation made on the disjointed distillation device are shown in Table 1.

TABLE 1

|  | Example | | | Comparative Example | | |
|---|---|---|---|---|---|---|
|  | 2 | 3 | 4 | 1 | 2 | 3 |
| Entrainer | toluene | → | → | → | → | → |
| Temperature of Bottom Product (° C.) | 93 | 89 | 96 | 89 | 90.5 | 91 |
| Composition of Bottom Product | | | | | | |
| Water (wt. %) | 0.05 | 0.3 | 0.04 | 0.8 | 0.5 | 0.7 |
| Entrainer (wt. %) | 8.2 | 12.2 | 6.6 | 5.5 | 4.5 | 2.9 |
| Results of Observation on Distillation Device | | | | | | |
| Flask at the bottom of Column | a | a | a | b | a | c |
| Packing in Column | a | a | a | d | e | c | a: No polymer was found.
b: A band polymer (width 2 mm, thickness 0.3 mm) was found in the vicinity of the liquid level.
c: After 5 hours, flooding took place; it was impossible to continue the test.
d: About 50 particles of polymer (2–3 mmφ) were found at the lower part of the packing layer.
e: About 20 particles of polymers (2–3 mmφ) were found on the surface of the packing.

EXAMPLES 5 and 6, and COMPARATIVE EXAMPLES 4 and 5

The procedure of Examples 1 to 4 was repeated except that use as the entrainer was made, instead of toluene, of methyl isobutyl ketone or isopropyl acetate. The results obtained are shown in Table 2.

TABLE 2

|  | Example | | Comparative Example | |
|---|---|---|---|---|
|  | 5 | 6 | 4 | 5 |
| Entrainer | methyl isobutyl ketone | isopropyl acetate | methyl isobutyl ketone | isopropyl acetate |
| Pressure at the Top of Column (mmHg) | 170 | 200 | 170 | 200 |
| Temperature of Bottom Product (° C.) | 96 | 93 | 90 | 100 |
| Composition of Bottom Product | | | | |
| Water (wt. %) | 0.1 | 0.3 | 0.9 | 0.1 |
| Entrainer (wt. %) | 5.5 | 7.6 | 0.23 | 2.4 |
| Results of Observation on Distillation Device | | | | |
| Flask at the bottom of Column | a | a | f | b |
| Packing in Column | a | a | f | d | a, b and d: See those to Table 1.
f: About 100 pop-corn-like polymer particles (2–3 mmφ) were found at the lower part of the packing layer.

What is claimed is:

1. In a process for producing acrylic acid, wherein propylene and/or acrolein is catalytically oxidized with molecular oxygen in a vapor phase and the gas resulting from the oxidation is cooled and/or absorbed in or scrubbed with water to form a crude aqueous acrylic acid, followed by azeotropic distillation for dehydration to remove water with an entrainer of a boiling point of no higher than 130° C. on the crude aqueous acrylic acid which may have, upon necessity, undergone removal of aldehydes contained therein to produce acrylic acid purified in that the crude aqueous acrylic acid is substantially dehydrated, the improvement which comprises conducting the azeotropic distillation under such conditions that concentrations of the entrainer and water in the bottom product of a distillation column for the azeotropic distillation for dehydration are from 5% to 30% by weight and no higher than 0.5% by weight, respectively.

2. The process of producing acrylic acid according to claim 1, wherein the concentration of the entrainer in the bottom product of the azeotropic distillation column for dehydration is from 6 to 15% by weight.

3. The process for producing acrylic acid according to claim 1, wherein the concentration of the water in the bottom product of the azeotropic distillation column for dehydration is from 0.05 to 0.3% by weight.

4. The process for producing acrylic acid according to claim 1, wherein the bottom product of the azeotropic distillation column for dehydration is subjected to separation therefrom of lower-boiling materials including acetic acid and the entrainer as a overhead product in a distillation column, which column will be hereinbelow referred to as a distillation column for separating acetic acid, thereby to obtain acrylic acid as the bottom product of the distillation column for separating acetic acid, the overhead product being returned to the azeotropic distillation column.

5. The process for producing acrylic acid according to claim 1, wherein the entrainer is azeotropically distilled with both water and acetic acid, and has a boiling point of 80 to 130° C.

6. The process for producing acrylic acid according to claim 1, wherein the temperature at the bottom of the azeotropic distillation column for dehydration and the temperature at the bottom of the distillation column for separating acetic acid are no higher than 100° C.

7. The process for producing acrylic acid according to claim 1, wherein the pressure at the top of the azeotropic distillation column for dehydration is 100 to 300 mmHg, and the pressure at the top of the distillation column for separating acetic acid is 50 to 200 mmHg.

8. The process for producing acrylic acid according to claim 1, wherein the theoretical number of plates of the azeotropic distillation column for dehydration and that of the distillation column for separating acetic acid are respectively 5 to 20.

9. The process for producing acrylic acid according to claim 1, wherein the crude aqueous acrylic acid fed to the azeotropic distillation column for dehydration contains 40% to 80% by weight of acrylic acid, 1% to 5% by weight of acetic acid, and 20% to 60% by weight of water.

10. The process for producing acrylic acid according to claim 1, wherein the overhead product of the azeotropic distillation column for dehydration, containing substantially the whole amount of the water, a portion of or the whole amount of the acetic acid, the water and the acetic acid being those originally contained in the crude aqueous acrylic acid, and the entrainer is separated into two phases, that is, an entrainer phase and an aqueous phase, and the whole amount of the entrainer phase is returned to the azeotropic distillation column for dehydration as reflux, while a portion of or the whole amount of the aqueous phase is re-used as the water for scrubbing in which the gas resulting from the oxidation reaction is absorbed.

11. The process for producing acrylic acid according to claim 1, wherein the entrainer is at least one solvent which boils at 80–130° C. and is selected from the group consisting of aliphatic and aromatic hydrocarbons and isobutylether and which azeotropically distills with both water and acetic acid.

12. The process for producing acrylic acid according to claim 1, wherein the entrainer is at least one solvent which boils at 80–130° C. and is selected from the group consisting of alkyl esters of acetic acid and methylisobutylketone and which azeotropically boils with water.

13. The process for producing acrylic acid according to claim 1, wherein the amount of the entrainer refluxed to the azeotropic distillation column for dehydration is 1 to 10 weight times the amount of water in the aqueous acrylic acid solution fed to the azeotropic distillation column.

14. The process for producing acrylic acid according to claim 1, wherein the azeotropic distillation column for dehydration is operated so that the bottom temperature is 100 to 60° C. and the top temperature is 30 to 60° C.

15. The process for producing acrylic acid according to claim 1, wherein the distillation column for separating acetic acid is operated so that the bottom temperature is 100 to 60° C. and the top temperature is 30 to 60° C.

16. The process for producing acrylic acid according to claim 1, wherein the azeotropic distillation column for dehydration is operated so that the concentrations in the bottom product of the entrainer is 6 to 15% by weight and of water is no higher than 0.3% by weight, respectively.

17. The process for producing acrylic acid according to claim 1, wherein no smaller than 50% of the lower boiling distillate leaving from the distillation column for separation of acetic acid is recycled to the azeotropic distillation column for dehydration.

18. The process for producing acrylic acid according to claim 1, wherein the distillation column for separating acetic acid is operated so that the acrylic acid removed from the bottom of the distillation column for separating acetic acid is acrylic acid so purified that its contents of acetic acid and of water are no higher than 0.1% by weight and no higher than 0.1% by weight, respectively.

* * * * *